United States Patent [19]
Pryor et al.

[11] Patent Number: 5,174,533
[45] Date of Patent: Dec. 29, 1992

[54] ADJUSTABLE INSTRUMENT MOUNTING ASSEMBLY

[75] Inventors: Jeffrey W. Pryor, Vista; Jack W. Ratcliff, Carlsbad; both of Calif.

[73] Assignee: Pryor Products, Oceanside, Calif.

[21] Appl. No.: 810,893

[22] Filed: Dec. 20, 1991

Related U.S. Application Data

[63] Continuation-in-part of Ser. No. 699,983, May 13, 1991, abandoned.

[51] Int. Cl.⁵ .................................................. A47F 5/00
[52] U.S. Cl. .............................. 248/288.5; 248/231.7; 403/90
[58] Field of Search .................. 248/229, 231.7, 288.3, 248/288.5, 125, 121, 122; 403/90, 97

[56] References Cited

U.S. PATENT DOCUMENTS

| | | | |
|---|---|---|---|
| 972,480 | 10/1910 | Southwick | |
| 1,303,345 | 5/1919 | McFeaters | |
| 1,372,431 | 3/1921 | Husi | |
| 1,573,272 | 2/1926 | Phillips | 248/288.5 |
| 1,964,626 | 6/1934 | Fotakis | 45/97 |
| 2,528,201 | 10/1950 | White | 248/226 |
| 2,554,544 | 5/1951 | Warner | 88/39 |
| 2,591,337 | 4/1952 | Cohen et al. | 248/226 |
| 3,442,478 | 5/1969 | Parapetti | 248/284 |
| 3,783,547 | 1/1974 | Bystrom | 403/90 X |
| 4,030,690 | 6/1977 | Hanauer | 248/125 X |
| 4,561,414 | 12/1985 | Nozato | 248/181 X |
| 4,666,111 | 5/1987 | Schuler | 248/231.7 X |
| 4,800,795 | 1/1989 | Yamashita | 84/421 |
| 4,832,294 | 5/1989 | Eidem | 248/125 |
| 4,832,299 | 5/1989 | Gorton et al. | 248/231.7 |
| 4,844,397 | 7/1989 | Shakoon et al. | 248/231.7 |
| 4,852,940 | 8/1989 | Kanigowski | 248/181 X |
| 4,903,929 | 2/1990 | Hoffman | 248/231.7 X |
| 4,974,802 | 12/1990 | Hendren | 248/288.5 X |
| 4,977,850 | 12/1990 | King | 248/125 X |

Primary Examiner—J. Franklin Foss
Attorney, Agent, or Firm—Brown, Martin, Haller & McClain

[57] ABSTRACT

An adjustable mounting assembly for mounting an instrument on a support member has a first clamping device for releasable clamping engagement with the support member and a second clamping device for securing to an instrument or piece of equipment, with a lockable, adjustable connection between the two clamping devices allowing adjustment about two perpendicular axes to allow the instrument orientation to be adjusted. In one version, an IV pole is secured at one end to the second clamping device, so that it can be oriented vertically or in any other selected orientation relative to a support member which may be vertical, horizontal, or in any other orientation. The pole can support other medical instruments such as IV pumps.

19 Claims, 3 Drawing Sheets

ADJUSTABLE INSTRUMENT MOUNTING ASSEMBLY

CROSS-REFERENCE TO RELATED APPLICATIONS

This application is a -Continuation-In-Part of application Ser. No. 07/699,983 filed May 13, 1991 now abandoned.

BACKGROUND OF THE INVENTION

The present invention relates generally to an adjustable mounting assembly for mounting instruments on a support post, and is particularly concerned with an assembly for mounting medical instruments on IV hanger poles and other convenient support members in a medical environment.

In the medical field, a large number of instruments are commonly used for both patient monitoring and treatment. Electronic instruments such as heart monitors are used to monitor various physical parameters, for example, while other instruments are used to deliver predetermined doses of medication to patients. Since these instruments are relatively fragile, they must normally be clamped to an appropriate support structure while in use to maintain the instrument in close proximity to the patient and avoid the risk of the instrument being inadvertently moved or dropped. Often, such instruments are secured to vertical support posts of the type used to hang IV (intra-venous) medication pumps.

Various clamping or locking devices have been devised in the past for holding such medical instruments on specific support structures, such as vertical IV hanger poles, table tops, bed rails and so on. However, these have often not provided the desired degree of adjustability in instrument orientation, for example to allow the care-giver to easily monitor the output readings on the display and to make adjustments as necessary, and also normally only allow the instrument to be secured to a support structure in a specific orientation, such as upright or horizontal.

In Gorton et al. U.S. Pat. No. 4,832,299, a clamp fixture is provided which has a first part for clamping onto a support such as an upright pole, and a second part rotatably connected to the first part for rotation about an axis transverse to the support pole and lockable in any selected orientation. The second part has arms for rotatably supporting medical instruments. However, any adjustment involves release and subsequent re-locking of two separate locking mechanisms, and is therefore relatively complex.

SUMMARY OF THE INVENTION

It is an object of the present invention to provide a new and improved adjustable mounting assembly for medical equipment and the like for adjustably holding such equipment on supporting members.

According to the present invention, an adjustable mounting assembly for holding an instrument on a support post is provided, which comprises a first clamping device for releasably clamping onto a support member and a second clamping device for releasable locking engagement with the first clamping device. One or more items of medical equipment are mounted on the second clamping device. The second clamping device is adjustably mounted on the first clamping device via an adjustment mechanism which allows the second clamping device to be rotated about two perpendicular axes of rotation to adjust its orientation relative to a support member on which the first clamping device is clamped.

In one embodiment of the invention, the second clamping device comprises an elongate clamping sleeve having a transverse clearance slot extending around part of its outer periphery, and a ball joint member is trapped in the sleeve with a stem projecting outwardly from the ball through the clearance slot for movement between the opposite ends of the slot. The stem is secured to the first clamping device. A pair of opposing jaw members are located in the sleeve on opposite sides of the ball member for releasable locking engagement with the ball member, one of the jaw members being biased by a releasable locking device between a locked position preventing relative movement between the ball member and sleeve, and a released position allowing relative rotational movement between the ball member and sleeve about two perpendicular axes, the sleeve being rotatable when released in a first direction about the axis of the stem and in a second direction about the axis of the sleeve, movement in the second direction being limited by the length of the slot.

When the locking device is backed off to release the jaw member, the orientation of an instrument or equipment relative to a support member can be adjusted easily, by rotating about the axis of the ball joint stem and tilting about the axis of the clamping sleeve until an optimum orientation is reached. At this point, the manually adjustable locking member is simply tightened to trap the ball joint member between the jaws, and the instrument will be securely locked in place. Since only one hand is needed to release or lock the jaws, the other hand can be used to support the equipment until locked in position, preventing slipping. The slot will prevent the equipment from banging against the support member if it is inadvertently dropped after releasing the jaws, since it can only slip a certain distance as limited by the length of the slot before the stem reaches the end of the slot, preventing any further downward rotation.

Preferably, the jaw members are of a suitable resilient material such as plastic, while the ball joint element is of metal, to provide a higher coefficient of friction between the parts which resists slipping. Even when the jaw is released, there will still be some engagement between the opposing jaws and ball joint member, which provides some frictional resistance against the instrument suddenly being released and dropping freely and rapidly. Additionally, the high coefficient of friction allows the ball to be locked without needing an excessively high clamping force.

In a preferred embodiment of the invention, the first clamping device comprises a C-clamp or vise, one arm of the C-clamp having a recess shaped for engagement with a shaft. An adjustable locking member extends transversely through the opposing arm for releasably locking a shaft or support member against the recess in the first mentioned arm. Preferably, the recess is shaped for engagement about either round or square cross-section shafts of various dimensions, or about the edge of a table, for example, and may include a round or V-shaped section and a flat or square corner section.

With this mounting assembly, equipment can be securely mounted on either a vertical or horizontal support shaft or even on the edge of a table, and can be easily rotated and tilted to the desired orientation, using one hand to support the instrument and the other to release and then re-secure the clamping sleeve to the ball joint member. Instruments such as medical monitoring and other instruments, or musical instruments such as percussion instruments, can be securely mounted at a convenient, adjustable orientation on any convenient support structure in this way.

In one embodiment of the invention, a medical instrument may be directly mounted on the second clamping device or sleeve via a mounting bracket. In an alternative embodiment, a short IV hanger pole is secured at one end to the second clamping device. Medical instruments such as IV pumps may then be mounted on the IV pole between the IV hooks and the mounting assembly, via suitable welded tabs or the like.

With the latter arrangement, an IV pole can be orientated vertically or in any other desired orientation relative to any support. Whatever the orientation of the support, whether vertical, horizontal, or other, the second clamping device can always be adjusted to achieve a vertical orientation of the attached IV pole by rotating it about the two axes of rotation. This allows an IV pole to be mounted in the most convenient position, for example adjacent a hospital bed, by clamping onto any convenient support such as a bed rail, bedside table, or the like.

BRIEF DESCRIPTION OF THE DRAWINGS

The present invention will be better understood from the following detailed description of some preferred embodiments of the invention, taken in conjunction with the accompanying drawings, in which like reference numerals refer to like parts, and in which.

DETAILED DESCRIPTION OF THE PREFERRED EMBODIMENTS

Figure 1:
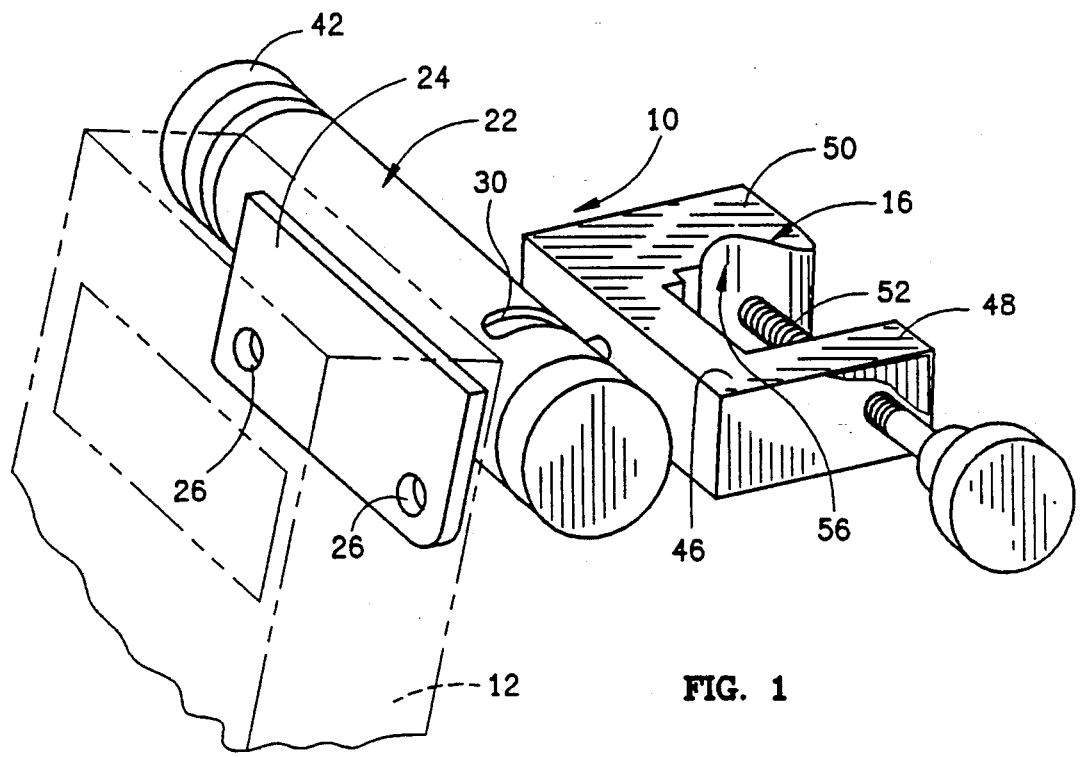
FIG. 1 is a perspective view of an adjustable mounting assembly according to a first embodiment of the invention for mounting an instrument on a support member.
Figure 2:
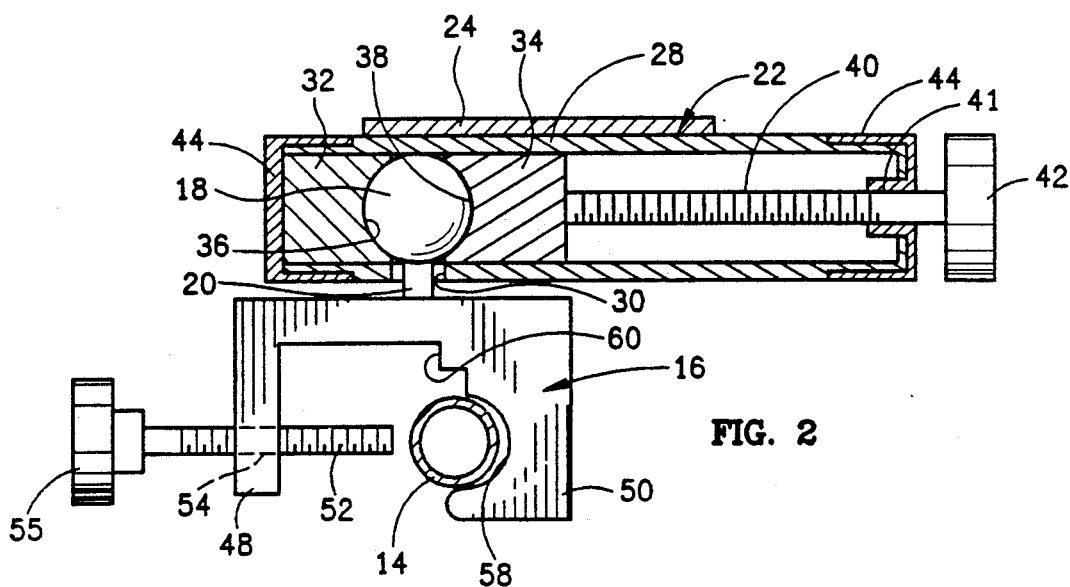
FIG. 2 is a top plan view of the device, partially in cross-section.

FIGS 1 and 2 of the drawings illustrate an adjustable mounting assembly 10 for mounting an instrument 12 on a support member such as an IV pole 14 or other support shaft, for example. Although in the preferred embodiments the mounting assembly is described as holding a medical instrument or medical equipment in a desired orientation, it may alternatively be used for securely holding other types of instruments where an adjustable angular orientation is required, for example for holding percussion instruments or photographic equipment.

The mounting assembly 10 basically comprises a first clamping device 16 for releasable clamping engagement with shaft 14 or other support structure, with a ball joint device or element 18 secured to the device 16 via stem 20, and a second clamping device 22 for releasable clamping engagement with the ball joint element 18. A suitable mounting bracket or plate 24 is secured to clamping device 22 for securing to a medical or other instrument 12, for example via screw type fasteners (not illustrated) extending through holes 26 provided on plate 24 for this purpose.

The clamping device 22 comprises an elongate clamping sleeve 28 having a transverse slot 30 extending partially around its periphery. The ball element 18 is trapped in sleeve 28 with the stem 20 projecting outwardly through slot 30. A pair of opposing clamping elements or jaws 32, 34 are mounted in the sleeve on opposite sides of ball joint element 18, the jaws each having a rounded recess 36, 38 on their inner faces for receiving opposite sides of ball joint element 18. One of the jaws 34 is adjustably mounted in the sleeve and can be moved back and forth via adjustment screw 40 which is secured at one end to jaw 34 and projects out through a threaded end nut 41 at the opposite end of sleeve 28. The screw 40 has an enlarged adjustment knob 42 at its outer end for manual locking and release of jaw 34. Removable ed caps 44 at opposite ends of sleeve 28 allow access to the interior of the sleeve for maintenance purposes.

Preferably, both jaws 32, 34 are of a resilient plastic material such as Delrin ® (Registered Trademark), PVC or other suitable plastics materials, while the ball joint member is of metal, to produce a high coefficient of friction between the parts to resist slipping when they are clamped together and also to provide some frictional resistance when they are released.

The clamping device 16 is of the C-clamp or vise type, comprising a generally C-shaped clamp member 46 having opposing arms 48, 50 and a locking screw member 52 extending through a screw-threaded bore 54 in one of the arms 48 to lock support member or shaft 14 against the opposing arm 50. Member 52 has an enlarged head or adjustment knob 55 at its outer end. Arm 50 has a recess 56 for locating or seating against shaft 14, as illustrated in FIG. 2. Preferably, the recess 56 has a first, rounded section 58 for locating against circular cross-section shafts or poles, and two square corner sections or indents 60 which can seat against square cross-section shafts or objects, for example the edge of a table top. The varying contour of the recess 56 allows the clamp 46 to be locked onto shafts and surfaces of various shapes and dimensions.

With this arrangement, an instrument 12 can be secured to a support member 14 such as an IV or other pole, for example, via a ball joint which permits rotation of the instrument relative to the support member about two perpendicular axes when released. When the ball joint element 18 is released by loosening locking screw 40, the clamping sleeve 28 can be freely rotated about the axis of ball joint stem 20 through 360°. Thus, the instrument 12 can be arranged to be upright or at any other desired angle, whether the support member 14 is vertical or horizontal. At the same time, the clamping sleeve can also be rotated about its own longitudinal axis by moving stem 20 along slot 30, the amount of rotation permitted being limited by the length of slot 30, in other words the angle subtended by this slot. The ends of slot 30 act as stops limiting the arc through which sleeve 28 can be rotated. Rotation of sleeve 28 about its longitudinal axis controls the angle of tilt of instrument 12, allowing it to be tilted to an easily visible or accessible angle, for example.

Once the instrument has been moved into the desired orientation, the adjustment screw is tightened to lock the jaw member 34 against ball member 18, preventing any further movement between the parts. Because of the high coefficient of plastic to metal frictional resistance, excessive clamping force is not necessary in order to ensure that the instrument is locked in place.

Additionally, in order to adjust the instrument from one position to another, adjustment screw may be backed off only slightly from the locked position, so that the ball member is still frictionally restrained against free slipping movement and the instrument does not immediately drop down when released. This reduces the risk of relatively heavy instruments falling freely and possibly damaging adjacent surfaces or instruments, or becoming damaged themselves. The operator also does not have to support the whole weight of the instrument as soon as it is released, but simply moves it to the desired orientation before locking down the adjustment screw again. The arrangement allows movement only about two perpendicular axes and traps the ball against movement relative to the clamping sleeve about any other axis.

The risk of the instrument falling or slipping freely when released, and potentially hitting against adjacent surfaces or against the support member 14 itself, is also reduced or eliminated by slot 30, which will stop the instrument from rotating downwardly as soon as stem 20 reaches the lowermost end of the slot. Preferably, the slot extends about half way around the periphery of sleeve 8, allowing rotation of sleeve through an angle of no more than 180° about its longitudinal axis.

The elongate clamping sleeve allows the adjustment knob 42 for locking or releasing the ball joint to project out to one side of the instrument, where it will be easily accessible to the user.

Figure 3:
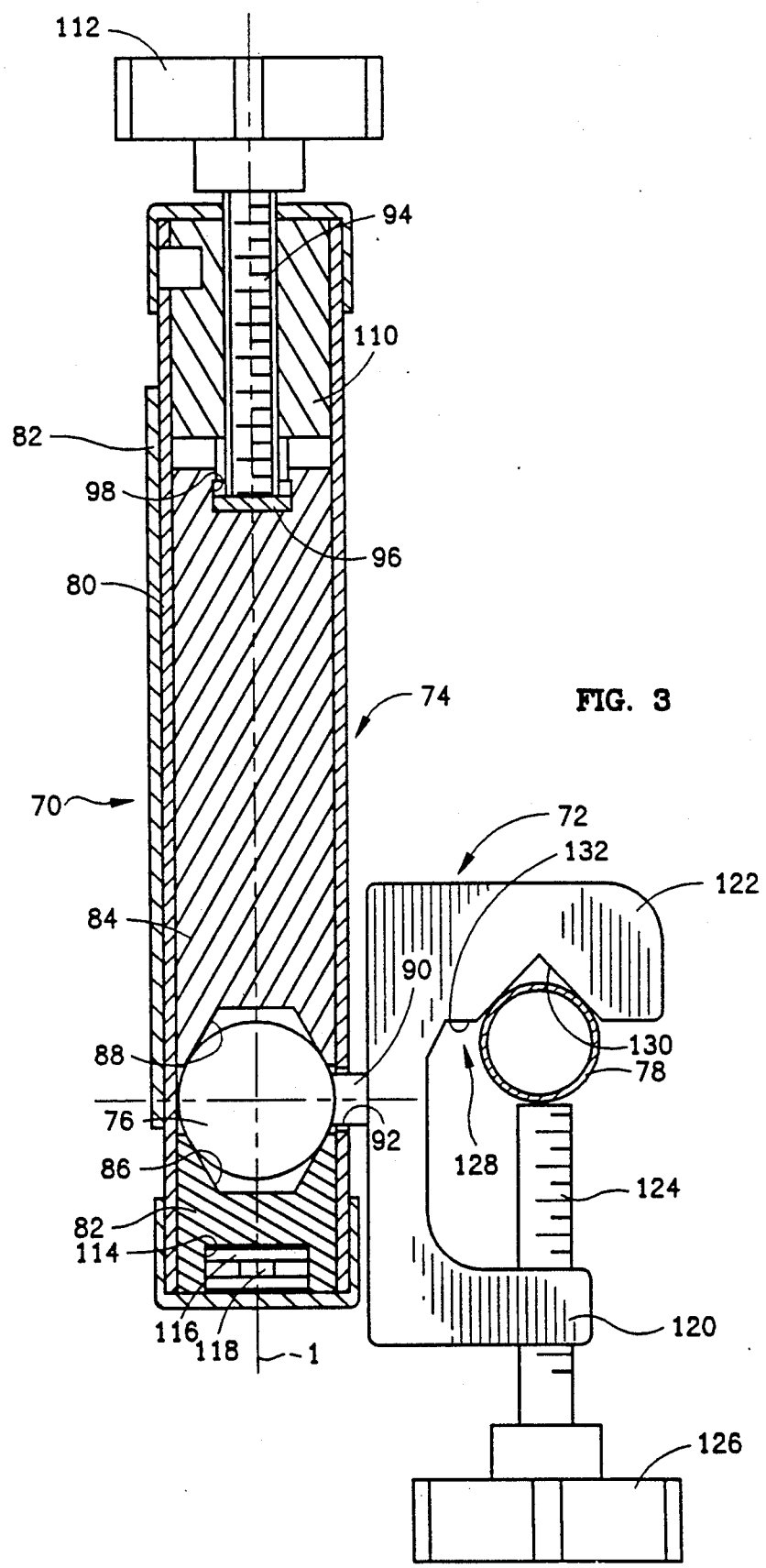
FIG. 3 is a view similar to FIG. 2 illustrating a modified embodiment of the invention.

FIG. 3 illustrates a modified adjustable mounting assembly 70 according to a second embodiment of the present invention. As in the first embodiment, mounting assembly 70 comprises first and second clamping devices 72, 74 adjustably secured together via a ball joint 76. The first clamping device 72 comprises a C-clamp or vise for clamping onto a support member such as a horizontal or vertical pole or shaft 78 or a table edge or other convenient support structure. The second clamping device comprises an elongate clamping sleeve 80 in which the ball joint 76 is trapped, clamping sleeve 80 carrying an attachment bracket 82 or other fastener device for securing it to an instrument to be supported.

The interior of the clamping sleeve 80 in this embodiment differs from the first embodiment. Ball joint 76 is located between opposing jaw or clamp members 82, 84 each having a frusto-conical shaped recess 86, 88, respectively, for seating against opposing sides of ball joint member 76. Ball joint stem 90 projects out of transverse slot 92 in sleeve 80, which is equivalent to slot 30 in the first embodiment, and preferably extends about halfway around the periphery of sleeve 80. One of the clamp members 82 is fixed in one end of the sleeve, while the other clamp member is biased by adjustment or locking screw 94 against ball joint or member 76. In this embodiment of the invention, locking screw 94 is not secured to the clamp member 84, but simply acts against a metal pressure plate 96 located in a recess 98 at the outer end of member 84. Locking screw 94 projects out of sleeve 80 through screw threaded nut 110 and has a suitable adjustment knob or head 112 at its outer end, as in the first embodiment. Fixed clamp member 82 also has a recess 114 at its outer end in which opposing spacers or pressure plates 116 are located, with a set screw 118 for controlling separation between plates 116 and thus the position of clamp member 82.

C-clamp member 72 is similar to C-clamp 46 of the first embodiment, and includes opposing arms 120, 122 with a locking screw 124 having a head 126 at one end projecting through a threaded bore in arm 120. However, the opposing arm 122 has a recess 128 for locating a support member which is of a different shape to that of the first embodiment. Recess 128 has a wide V-shaped section 130 instead of a round section, to accommodate a larger range of support pole or shaft diameters, and a straight or flat section 132 extending from the inner end of the V-shaped section for seating against square or flat support members.

Adjustment of an instrument orientation in this embodiment is equivalent to the previous embodiment, and will therefore not be described in detail. However, since the locking screw 94 is not physically attached to clamp member or jaw 84, it does not pull member 84 away from the ball joint but simply reduces the pressure acting against the ball joint. Thus, there will be more frictional resistance against slipping of the instrument on release of locking screw 94 in this embodiment than in the previous embodiment, where the clamp member was moved away from the ball member. Thus, even if the instrument is unsupported when screw 94 is backed off, it will not suddenly drop down or move, but will slip slowly downwards. When the ball joint is released, the clamping sleeve can be rotated about the two perpendicular axes 134, 136 of sleeve 80 and stem 90, as in the previous embodiment, with the degree of rotation permitted around axis 134 being limited by the length of slot 92.

As in the first embodiment, the clamp members 82, 84 are both of a suitable plastics material such as PVC or Delrin ®, while the ball member 76 is metal to provide a relatively high coefficient of friction between the parts so that excessive clamping force does not have to be applied in order to securely lock an instrument in a selected position, and also to reduce the rate of slipping when the ball member is released.

Figure 4:
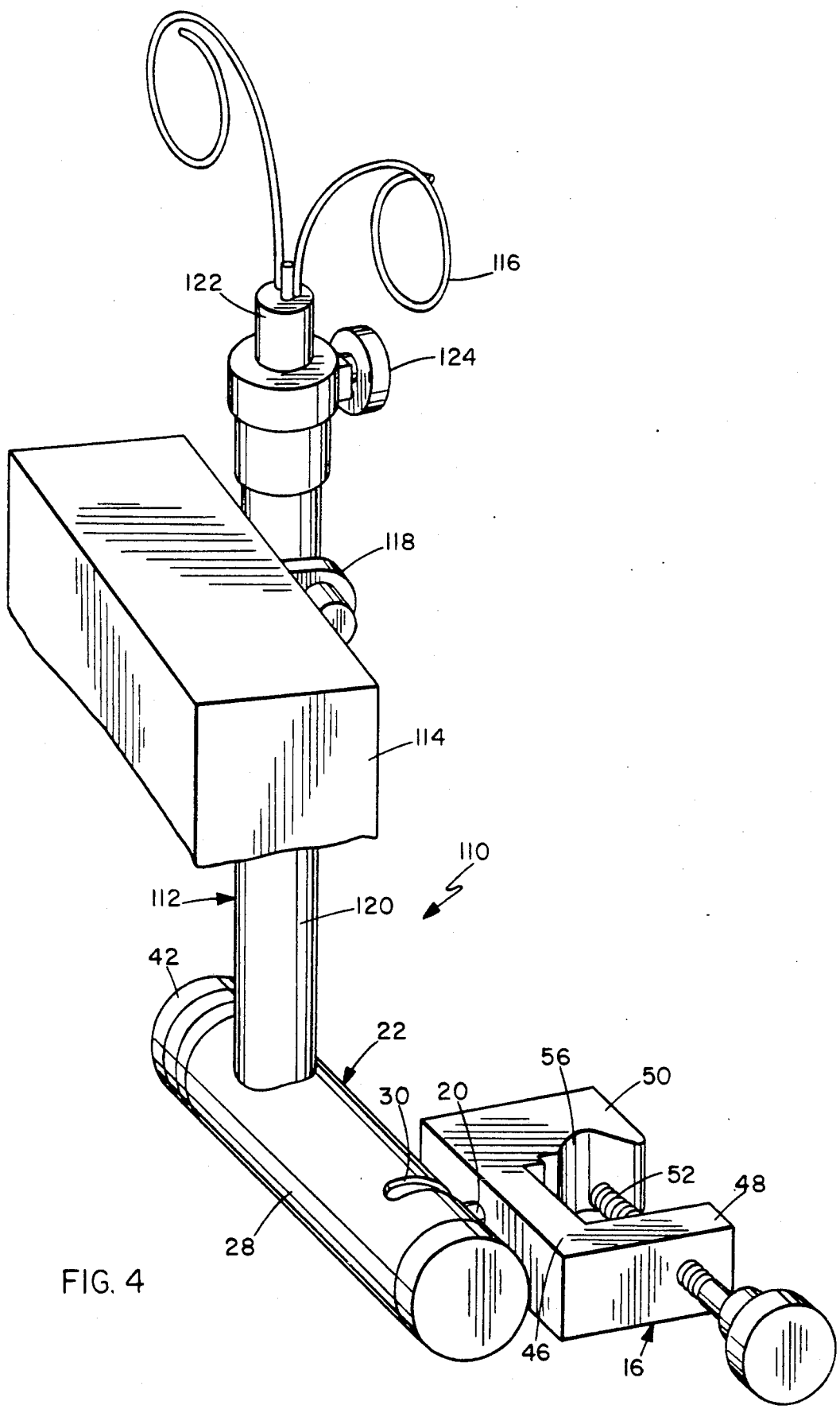
FIG. 4 is a perspective view of an adjustable mounting assembly according to another embodiment of the invention.

FIG. 4 illustrates an adjustable mounting assembly 110 according to another embodiment of the invention. The mounting assembly 110 in this embodiment is similar to that of FIGS. 1 and 2, and like reference numerals have been used where appropriate. The interior of sleeve 28 in the embodiment of FIG. 4 will be identical to that of the first embodiment, as illustrated in FIG. 2, and will therefore not be described in detail. However, in the embodiment of FIG. 4, a short IV pole 112 is secured at one end to the clamping sleeve 28, and the mounting bracket 24 is eliminated since any medical instruments such as IV pump 114 may be mounted directly on the short IV pole 112 between the IV bottle hangers or hooks 116 at one end and the sleeve 28 at the other end. The pole 112 may be permanently secured to sleeve 28 by welding or the like, as in the illustrated embodiment, or may be releasably mounted on the sleeve by any suitable releasable fastener mechanism.

Any type of IV pump or other medical instrument can be readily mounted on pole 112 by any suitable fastener mechanism, for example a screw-on clamp 118 for clamping onto the pole with a suitable welded-on bracket or tabs for attachment of the IV pump 114 or other device. More than one instrument may be mounted on pole 112 if necessary. The IV pole is in two telescopically-engaging parts 120, 122, so that the length of the pole can be adjusted. A suitable locking mechanism 124 is provided for locking the pole at the desired extension of the upper part 122 out of lower part 120.

With this arrangement, an IV hanger can be supported from any suitable support rod or surface, such as a vertical or horizontal bed rail, a side table, or any other surface or shaft at any orientation between horizontal and vertical, at the most convenient location for access to a patient. The first clamping device 16 is simply clamped onto the selected support, and the ball element within sleeve 28 is released to allow the pole to be adjusted to the desired orientation relative to the support, for example a vertical orientation. This is done by rotating sleeve 28 about the axis of shaft 20, and rotating the pole 12 about the axis of sleeve 28 until the desired orientation is reached. At this point, adjustment knob 42 is tightened to clamp the pole 112 in the desired orientation. Other alternative clamping mechanisms for allowing rotation about at least two perpendicular axes may be used in place of the ball joint and clamping jaws as illustrated in FIG. 2, such as the assembly of FIG. 3 or a universal joint.

This arrangement allows an IV pole to support more weight in a stable manner without having to stand it on the floor next to a bed, for example, where the base of the pole would take up needed space and may obstruct access to a patient. By clamping the pole on any convenient adjacent support surface, which holds the equipment at the desired location but without impeding access to a patient, these problems are reduced or avoided. The adjustable mounting assembly allows any convenient support or mounting surface, whether oriented vertically, horizontally, or at any angle in between, to be used to mount the assembly, while allowing the pole to be adjusted to a vertical orientation, or any other desired orientation, relative to the first clamping device, quickly and easily once the assembly is mounted, simply by releasing a single locking device and then moving the pole to the desired orientation before re-locking the device. For example, FIG. 4 illustrates the first clamping device orientated to clamp onto a vertical surface or shaft, with pole 112 oriented vertically. If the clamping device 16 was instead clamped onto a horizontal surface or shaft, the pole 120 and attached sleeve 28 would simply be rotated 90° from the illustrated position so that sleeve 28 is horizontal while pole 120 projects vertically upwards. Slot 30 allows tilting of the pole.

Although some preferred embodiments of the invention have been described above by way of example only, it will be understood by those skilled in the field that modifications may be made to the disclosed embodiments without departing from the scope of the invention, which is defined by the appended claims.

We claim:

1. An adjustable mounting assembly, comprising:
   a first clamping device for releasably clamping onto a selected support member in any orientation from vertical to horizontal;
   a second clamping device for releasable locking engagement with the first clamping device, the second clamping device comprising a ball-shaped element secured to said first clamping device, a clamping member having clamping jaws for releasable clamping engagement with said ball-shaped element at a desired orientation of said clamping member relative to said first clamping device for adjusting the orientation of the clamping member relative to the first clamping device about two perpendicular axes of rotation, and locking means for releasably locking the clamping member in the desired orientation; and
   mounting means for mounting medical equipment on said clamping member, whereby the equipment can be oriented in a desired orientation relative to a support member in any orientation from vertical to horizontal.

2. The assembly as claimed in claim 1, wherein said mounting means includes a pole secured at one end to project transversely from said clamping member means comprising means for allowing said pole to be orientated in a desired orientation relative to any support member on which the first clamping device is clamped.

3. The assembly as claimed in claim 1, wherein the ball joint device comprises a ball element and a stem projecting from the ball element, the stem being secured to said first clamping device at its free end, and the clamping member comprises an elongate clamping sleeve having a slot extending around part of its periphery in a direction transverse to the longitudinal axis of the sleeve, the ball element being located in the sleeve with the stem projecting out through said slot, said clamping jaws comprising a pair of opposing jaw members in said sleeve on opposite sides of said ball element.

4. The assembly as claimed in claim 3, wherein said mounting means comprises a pole secured at one end to said sleeve and projecting transversely from said sleeve.

5. The assembly as claimed in claim 4, wherein said pole has IV hanger hooks at its opposite, free end, and mounting means intermediate its ends for mounting medical instruments on said pole.

6. An adjustable mounting assembly, comprising:
   a first clamping device for releasably clamping onto a selected support member in any orientation from vertical to horizontal;
   a second clamping device for releasable locking engagement with the first clamping device, the second clamping device including adjustment means for adjusting the orientation of the second clamping device relative to the first clamping device about two perpendicular axes of rotation, and locking means for releasably locking the second clamping device in the desired orientation;
   mounting means for mounting medical equipment on said second clamping device, whereby the equipment can be oriented in a desired orientation relative to a support member in any orientation from vertical to horizontal;
   said mounting means including a pole secured at one end to project from said second clamping device, said adjustment means comprising means for allowing said pole to be orientated in a desired orientation relative to any support member on which the first clamping device is clamped; and
   the pole having IV hanger hooks at its free end, and a mounting surface intermediate its ends for allowing medical instruments to be mounted on the pole.

7. The assembly as claimed in claim 6, wherein the second clamping device comprises a ball joint device secured to the first clamping device, and a clamping member having clamping jaws for releasable clamping engagement with said ball joint device at a desired orientation of said clamping member relative to said first clamping device.

8. An adjustable mounting assembly for holding an instrument on a support member, comprising:
   a first clamping device for releasable clamping engagement with a support member;
   a ball joint device secured to the first clamping device, the ball joint device comprising a ball element and a stem projecting from the ball element, the stem being secured to the clamping device at its free end;

a second clamping device for releasable clamping engagement with said ball element, the second clamping device comprising an elongate clamping sleeve having a slot extending around part of its periphery in a direction transverse to the longitudinal axis of the sleeve, the ball element being located in said sleeve with said stem projecting outwardly through said slot, and a pair of opposing jaw members in said sleeve on opposite sides of said ball element;

a locking device acting on a first one of said jaw members, the locking device being movable between a first position biasing said first jaw member into locking engagement with said ball element and a second position releasing said first jaw member; and a mounting device on said clamping sleeve for securing an instrument to said sleeve.

9. The assembly as claimed in claim 8, wherein said ball element and jaw members are of different materials having a high coefficient of friction.

10. The assembly as claimed in claim 9, wherein said ball element is of metal and said jaw members are of plastic material.

11. The assembly as claimed in claim 8, wherein said jaw members have at least partially rounded recesses on their innermost ends for seating against opposite sides of said ball element.

12. The assembly as claimed in claim 8, wherein said first jaw member comprises an elongate, solid cylindrical member slidably mounted in said clamping sleeve.

13. The assembly as claimed in claim 8, wherein said mounting device comprises a flat attachment bracket facing away from said slot and having holes for receiving fastener devices for securing said bracket to an instrument.

14. The assembly as claimed in claim 8, wherein said first clamping device comprises a C-shaped member having opposing first and second arms, the first arm having a recess for seating against a support member, and an adjustable locking member projecting through the second arm for locking a support member against said first arm.

15. The assembly as claimed in claim 14, wherein said recess has a varying contour for location against round and rectangular shaped support members.

16. The assembly as claimed in claim 15, wherein said recess has a V-shaped section and a flat section.

17. The assembly as claimed in claim 8, wherein said slot extends around approximately half of the periphery of said sleeve.

18. An adjustable mounting assembly for releasably holding a device on a support, comprising:

first clamping means for releasable clamping engagement with a support member;

a ball member having a stem, the stem being secured to said first clamping means;

second clamping means for releasable clamping engagement with said ball member;

said second clamping means comprising an elongate clamping sleeve having a transverse slot extending around part of its periphery, said ball member being trapped in said sleeve with said stem projecting through said slot for movement between opposite ends of the slot, and jaw means in said clamping sleeve for releasable locking engagement with said ball member, said jaw means being movable between a locking position in which said ball member is trapped and a released position in which clamping sleeve can move relative to said ball member in a first rotational direction about the axis of said stem and a second rotational direction about the axis of said sleeve, rotation about the axis of said sleeve being limited by the length of said slot; and a mounting pole secured at one end to the clamping sleeve to project transversely from the sleeve, the mounting pole having mounting means for allowing selected items to be mounted on the pole.

19. An IV stand, comprising:

a pole;

support means at one end of the pole for suspending at least one IV bag from the pole;

adjustable clamping means secured to the opposite end of the pole for releasably mounting the pole on selected support member at any orientation from vertical to horizontal, the clamping means comprising a first clamping part for releasable clamping engagement with a selected support member and a second clamping part adjustably mounted on the first part for adjusting the orientation of said second clamping part relative to the selected support member, said pole being secured to said second clamping part, said second clamping part including releasable locking means for releasably locking said second clamping part in a selected orientation relative to said first clamping part; and mounting means intermediate the ends of the pole for allowing a medical instrument to be mounted on the pole.

* * * * *

UNITED STATES PATENT AND TRADEMARK OFFICE
CERTIFICATE OF CORRECTION

PATENT NO. : 5,174,533
DATED : December 29, 1992
INVENTOR(S) : Jeffrey W. Pryor, et al.

It is certified that error appears in the above-identified patent and that said Letters Patent is hereby corrected as shown below:

Column 8, claim 2, line 6, after "member"

insert a period (.) and delete the rest of the claim.

Signed and Sealed this

Thirtieth Day of November, 1993

Attest:

BRUCE LEHMAN

Attesting Officer

Commissioner of Patents and Trademarks